US005998157A

United States Patent [19]

Schmitt et al.

[11] Patent Number: 5,998,157

[45] Date of Patent: Dec. 7, 1999

[54] ACYLATED PROTEIN AGGREGATES AND THEIR USE AS SIGNAL ENHANCERS IN AN IMMUNOASSAY FOR THE DETECTION OF ANTIBODIES

[75] Inventors: Urban Schmitt, Oberhausen; Dittmar Schlieper, Weilheim; Franz Schmid, Diessen, all of Germany

[73] Assignee: Roche Diagnostics GmbH, Mannnehim, Germany

[21] Appl. No.: 08/505,290

[22] PCT Filed: Dec. 21, 1994

[86] PCT No.: PCT/EP94/04265

§ 371 Date: Feb. 29, 1996

§ 102(e) Date: Feb. 29, 1996

[87] PCT Pub. No.: WO95/17427

PCT Pub. Date: Jun. 29, 1995

[30] Foreign Application Priority Data

Dec. 21, 1993 [DE] Germany ............................ 43 43 480

[51] Int. Cl.$^{6}$ .................................................... G01N 33/53

[52] U.S. Cl. ......................... 435/7.94; 435/7.92; 435/7.2; 435/7.1; 530/363; 530/362

[58] Field of Search ................................ 435/7.94, 7.92, 435/7.2, 7.1; 530/363, 362

[56] References Cited

PUBLICATIONS

Dorder et al, Chem. Abs., vol. 119, 188678p (Equivalent to WO 93/16,735), 1993.

Medi–Physics, Inc., MPI MAA KIT, Oct. 1990.

*Primary Examiner*—Ponnathapura Achutamurthy
*Assistant Examiner*—T. D. Wessendorf
*Attorney, Agent, or Firm*—Nikaido Marmelstein Murray & Oram LLP

[57] ABSTRACT

The invention addresses protein aggregates that are acylated with —CO— R groups, wherein R is a branched or non-branched C1–C4 alkyl residue which can be substituted with hydroxy, carboxy, $SO_3H$ or $PO_3H_2$ groups. These protein aggregates can be used to increase the intensity of signals and avoid false-positive results in immunoassays for the detection of antibodies. The inventions also adresses a reagent with a buffer and a binding reagent with an immunological binding partner containing said protein aggregate.

9 Claims, 3 Drawing Sheets

INFLUENCE OF ACETYLATED TBSA ON THE SIGNAL OF HCV-POSITIVE SERA

INFLUENCE OF ACETYLATED TBSA ON THE SIGNAL OF HCV-POSITIVE SERA

INFLUENCE OF ACETYLATED TBSA ON THE SIGNAL OF HCV-POSITIVE SERA

ACYLATED PROTEIN AGGREGATES AND THEIR USE AS SIGNAL ENHANCERS IN AN IMMUNOASSAY FOR THE DETECTION OF ANTIBODIES

The invention addresses acylated protein aggregates, their manufacture, and their use in an agent and in a reagent for immunological assays, and their use as signal enhancers in immunoassays for the detection of antibodies and a corresponding immunological detection method.

Immunological detection methods have gained great importance over the last years. This serves to detect the presence of drugs, hormones, proteins, and especially infectious organisms in biological samples in a rapid and exact manner. In all immunological detection methods, there is a specific binding reaction between a first specific binding partner, the substance to be detected (analyte) and a second specific binding partner which specifically reacts with the ligand and binds it. Ligand and specific ligand-binding partner form a specific binding pair, generally a complex between an antigen and an antibody or antibody fragment. It is possible that more than one ligand or one binding partner react with each other in each reaction. These specific binding reactions are detected in various ways. Generally, one participant in the specific binding reaction is labeled. Conventional labeling methods make use of radio-isotopes, chromogens, fluorogens, or enzymatic labels. In heterogeneous immunoassays, one of the binding partners is immobilized on a solid phase.

The detection of specific antibodies that are directed against an antigen in an heterogeneous immunoassay, especially so-called sandwich immunoassays, is generally accomplished such that in a first incubation step, a solid phase bound antigen is brought into contact with the sample to be assayed, usually human serum or plasma. During incubation, the antibodies to the antigen contained in the sample bind to the wall-bound antigen. After the reaction, the test mixture is washed and in a second reaction step, the solid phase bound antibodies are detected with the aid of a second antibody that bears a label and is against the antibody class to be determined. This detection is accomplished in that a labeled antibody (monoclonal or polyclonal) directed against the antibody class to be determined or a labeled analyte analog bind in a second incubation step to the antibodies that have bound the wall-bound antigen in the first incubation step. If IgG antibodies are to be detected, it is preferred to use a labeled anti-IgG; if IgM antibodies are used, an anti-IgM antibody is preferred. After the second incubation step, the test mixture is washed and the non-bound, excess labeled anti-antibodies or analyte analogs are removed. In a third step, the amount of bound antibody is detected such that, for example, in an enzyme immunoassay the test mixture reacts with a substrate solution and the resulting coloration is photometrically measured. The absorbance or the signal of this coloration is proportional to the amount of bound antibody.

In a particular embodiment of these antibody immunoassays, the antigen is not directly bound to the solid phase, but is bound to the solid phase before or preferably during the assay via another specific binding partner. In a preferred manner, an antigen to which biotin is covalently linked, binds to a streptavidin-coated solid phase.

A particular type of interference in antibody tests has been noticed especially during the detection of IgG antibodies to an antigen, e.g. HIV, HCV, toxoplasmosis antibodies and the like. If the same amount of a sample of the human serum containing a high concentration of an antibody directed against an antigen (e.g. antibodies to HCV) is diluted with different sera which do not contain an antibody to this antigen, there are significant differences in the recovery of the antibody amount in the so-diluted sera, although all sera contain the same total amount of specific antibodies. In the enzyme immunoassays, the samples diluted with sera produce a signal that was by a factor of 2–10 too low. An explanation for this phenomenon is not known, but it could possibly be that human sera contain substances which interfere with the binding of specific antibodies to an antigen. Another or additional explanation could be that these substances contained in human sera interfere with the detection of bound antibodies in the second incubation step. This drastic signal reduction caused by serum components is particularly critical when weakly positive sera are assayed which in an unfavorable case are found to be negative and, hence, lead to an incorrect diagnosis.

It was, hence, an object of the present invention to achieve a sufficiently high signal increase in an immunoassay for the detection of antibodies so that false-negative analysis results are reduced or avoided. The object is accomplished by use of specifically acylated protein aggregates in immunoassays.

Subject matter of the invention are protein aggregates as substances to increase the signal intensity in immunoassays for the determination of antibodies, said substances being acylated with —CO—R groups wherein R is a branched or unbranched C1–C4 alkyl residue which can be substituted with carboxy, hydroxy, $SO_3H$, or $PO_3H_2$ groups.

Another subject matter of the invention is a corresponding means to increase the signal intensity in immunoassays comprising a buffer, and one or several of the substances in accordance with the invention to increase the signal intensity.

Another subject matter of the invention is a specific binding reagent for immunoassays for the determination of antibodies, comprising a binding partner for the antibody to be determined, characterized in that it contains an additional one or several of the substances of the invention or means to increase the signal intensity in the immunoassay.

Yet another subject matter of the invention is a method to increase the signal and to reduce false-negative analysis results in immunoassays for the determination of antibodies by bringing a substance in accordance with the invention or the means for increasing the signal in accordance with the invention in contact with the specific binding partners directed against the antibody, especially the unlabeled binding partners.

A particular subject matter of the invention is a method for determining an antibody in a sample while the signal is increased and false-negative analysis results are reduced by means of contacting the sample to be assayed for the antibody with one or several specific binding partners of the antibody, wherein at least one binding partner is labeled forming a detectable binding pair with the antibody, measuring the signal of the labeled binding pair or the free labeled binding partner as a measure for the presence or concentration of the antibody in the sample, characterized in that there is added to the sample or one of the specific binding partners a protein aggregate which is acylated with —CO—R groups, wherein R is a branched or unbranched C1–C4 alkyl residue, which can be substituted with carboxy, hydroxy, $SO_3H$, or $PO_3H_2$ groups.

Samples are generally body fluids such as blood, serum or plasma, saliva, urine, or other body fluids, especially serum or plasma.

The antibodies to be detected are all antibodies directed against an antigen, especially immunoglobulin antibodies.

A specific binding partner can be any biological or chemical binding partner which reacts specifically to the antibody to be determined of a specific binding pair. These are especially antigens, haptens, and anti-antibodies.

At least one of the specific binding partners in an immunoassay is labeled. The labeling can furnish a measurable signal, either directly or indirectly, e.g. through radioactivity, chemiluminescence, phosphorescence, fluorescence, or electrochemiluminescence, or a visible color. The specific binding partner can also be indirectly detectable, e.g. as an enzymatic label, biotin, or avidin label, which participate in one or several reactions in order to generate a detectable substance. Enzymatic labels are preferred, especially peroxidase, glucose oxidase, β-galactosidase, or electrochemiluminescent labels. The present invention preferably makes use of a labeled anti-antibody to the antibody to be detected.

Substances to increase the signal in accordance with the invention are acylated protein aggregates. A protein aggregate is understood to be an aggregate that was polymerized from identical or different defined protein monomers to form a high molecular particle. Per definition, a protein aggregate is understood to be an artificial particle consisting of at least 2, preferably 3–40,000, particularly preferred 30–600 protein monomers that are bound to each other in such a tight manner that they do not decompose into individual molecules in aqueous solution. In a preferred manner, the protein aggregates are soluble in water.

Polymerization aggregation of proteins can be accomplished in thermal or chemical procedures.

In thermal polymerization procedures, protein monomers are combined into aggregates by applying higher temperatures. The thermal polymerization of proteins is described in EP-A-269 092, where albumin is used.

The chemical polymerization of protein monomers is accomplished with non-protein-containing homo- or hetero-bifunctional linker molecules. These procedures for linking proteins are known to the experts and are described in GB-A 1505 400, EP-A-0 122 209, or EP-A 269 092, for example. Examples for the linking of protein monomers to heterobifunctional linkers are reactions with bis(maleinimido)-methylester, dimethylsuberimidate, disuccinimidyl-suberate, glutardialdehyde, N-succinimidyl-3-(2-pyridyldithio)propionate, N-5-azido-2-nitrobenzoylsuccinimide, N-succinimidyl(4-iodine acetyl)-aminobenzoate or the combination of maleinimidohexanoyl-N-hydroxysuccinimide ester (MHS) or maleinimido-benzoyl-NHS (MBS) and N-succinimidyl-3-acetyl-thiopropionate (SATP). Examples for homobifunctional linkers include diaminohexane, carbodiimide, and others.

In a preferred manner, the method of the invention makes use of protein polymers that were combined to aggregates in a thermal procedure. Albumin, preferably a serum albumin, especially bovine serum albumin (thermo-BSA) that was thermally polymerized and then acylated, particularly acetylated or succinylated is particularly preferred. A non-acylated thermo-bovine serum albumin is described in EP-A 269 092.

Advantageously, polymerization is accomplished and controlled such that polyprotein aggregate particles of a certain largely uniform size are generated. A particle size of 10–200 nm, particularly advantageous between 20 and 50 nm is preferred. This corresponds to a molecular weight of 240,000 Da–$2.2\times10^9$ Da, particularly preferred $2.2\times10^6$–$35\times10^6$ Da. The particle size can be determined in commonly known procedures such as PCS (Photon Correlation Spectroscopy). If necessary, the particle size range that is particularly suitable for the invention can be separated from a raw polymerisate mixture by means of gel filtration in order to obtain a particularly uniform particle size.

The protein monomers used for the polymerization can either be identical or different. It is preferred to polymerize uniform protein monomers. Albumin monomers are particularly suitable. Possible albumin monomers are all animal or human albumins, especially serum albumins. Bovine serum albumin (BSA) is particularly suitable for the invention.

In accordance with the invention, the protein aggregates are acylated with CO—R groups wherein R is a branched or unbranched C1–C4-alkyl residue, which can be substituted with carboxy, hydroxy, $PO_3H_2$ or $SO_3H$. A particularly preferred substituent is the carboxy group.

The acyl groups can be either included in the protein monomers or in the protein aggregates after polymerization of the protein monomers. Acylation of proteins is accomplished in accordance with known methods, preferably with acylanhydrides or with acyl-O-succinimide. Acetylated or succinylated protein aggregates have proven to be particularly advantageous, especially albumin aggregates (R=methyl and/or $CH_2$—$CH_2$—COOH). Acetic acid-O-succinimide is preferred for acetylation. Succinic acid anhydride is preferably used for succinylation.

In the acylation process, essentially free amino groups (e.g. lysin residues) of the protein aggregate are acylated. The term acylated protein aggregates means that at least one of the present free amino groups is acylated. The nearly complete acylation of all free amino groups is, however, preferred.

Another subject matter of the invention is an agent for reducing interference in immunological tests, comprising a buffer for immunological tests and the substance in accordance with the invention for reducing interference. Possible buffers are all aqueous buffers which are conventionally used in immunoassays, including phosphate, glycine-HCl, or glycine-NaOH, acetate, carbonate, citrate or organic buffers, such as imidazole/HC; triethanolamine; MES=(4-morpholinoethane sulfonic acid), TRIS=(TRIS (hydroxymethyl)-aminomethane), HEPES=(4-(2-hydroxy-ethyl)-1-piperazine ethane sulfonic acid), MOPS (3-N-morpholino-propane-sulfonic acid) and other similar buffers. The pH value and the concentration of the buffer salts depend on the immunoassay involved, e.g. and also on the enzyme used for the enzymatic label. Usually, the pH values range between 4 and 9. Conventional buffer concentrations are between 1 mM and 1 M.

The concentration of the substance for reducing interference on the amount of immunological test components and the interfering components contained therein with which the agent for reducing said interference is brought into contact. In conventional immunoassays, the concentration of interference-reducing substance in the interference-reducing agent should be so high as to have a concentration between 1 mg per ml and 50 mg per ml, preferably 5 mg per ml and 20 mg per ml after contact with the immunological test components, especially the unlabelled biotin partner. In individual cases, concentrations up to 200 mg per ml may also be necessary.

In addition, the interference-reducing agent of the invention can also contain additional substances such as preservative agents and the like. For use in an immunoassay, the interference-reducing agent is advantageously present in an aqueous buffer solution. Moreover, it is also possible to use it to impregnate a porous carrier material (fleece), e.g. on a test strip and its storage in a solid form, e.g. as a lyophilisate.

Another subject matter of the invention is a specific immunological binding reagent with a partner of a specific binding pair, and the interference-reducing substance or interference-reducing agent in accordance with the invention.

In accordance with the present invention, the binding reagent is obtained such that one or several of the specific binding partners of an immunoassay and at least one interference-reducing substance or interference-reducing agent in accordance with the invention are mixed together. Optionally, additives such as preservatives or stabilizers or the like may be added. The amount of specific binding partner depends on the immunoassay used, the amount of partner to be bound, the type of label used and other factors. Generally, the concentration ranges between 1 and 20 μg/ml.

The amount of acylated protein aggregates in the binding reagent advantageously ranges between 1 mg/ml and 50 mg/ml, preferably between 5 and 20 mg/ml. In isolated cases, concentrations up to 200 mg/ml may also be necessary.

The specific binding reagent can be employed in any homogeneous or heterogeneous immunoassay where a specific binding partner is useful for the detection of the presence or absence of a specifically binding ligand. Examples include sandwich assays, competitive immunoassays and other immunoassays known to the expert. The tests can be carried out in solutions or on solid carriers.

Generally, the immunoassay in accordance with the invention is carried out such that a sample containing the ligand is brought into contact with the specific binding reagent that is in solution in accordance with the present invention. A specific binding complex then forms directly or indirectly between the antibody and the specific binding partner. The antibody and the binding partner can directly form a complex. The binding partner is then specific for the ligand. However, it is also possible that the binding partner forms indirectly via one or several specific binding molecules a complex with the ligand, and these binding molecules then bind with the antibody.

If the method is carried out as a heterogeneous immunoassay on solid carriers, e.g. tubes, microtiter plates or a test carrier, a specific binding partner for the antibody can be directly immobilized on the carrier. However, it is preferred that a specific binding partner for the antibody binding partner be immobilized on the carrier. A preferred example is immobilized streptavidin as a specific binding reagent for biotinylated binding partners. The various variants of such heterogeneous immunoassays are known to the expert.

In competitive immunoassays, the antibody and the labelled antibody analog compete for the non-labelled ligand-binding partners, which can bind to the solid phase via a second binding site, preferably a specific binding site such as biotin, as is the case in heterogeneous immunoassays. The labelling of free and bound antibody analogs is used as a measure for the presence or the amount of ligand to be determined.

In sandwich immunoassays, the ligand binds with a first specific binding site to a labelled binding partner and with the second binding site to an unlabelled ligand binding partner, which has another specific binding site for the solid phase, as is the case in heterogeneous immunoassays. A complex then forms between antibodies, labelled and unlabelled binding partners. In heterogeneous tests, the complex binds to the solid phase via the unlabelled binding partner and can be separated from the free labelled binding partner by means of washing, for example. Free or bound labelled ligand-binding partners are determined as a measure for the presence or the amount of the ligand to be determined according to known methods. When enzymatic labels are used, a color-forming enzyme substrate is added to the labelled species and the resulting coloration is measured.

The substances of the invention demonstrate their effect in a particularly advantageous manner in sandwich immunossays, especially in hetergeneous sandwich immunoassays.

Experience has shown that the effect of the substances in accordance with the invention is influenced in a particularly advantageous manner when the sample with the unlabeled binding partner is incubated together with an acylated albumin aggregate of the invention in solution, and when the labeled binding partner is added after this step.

Another subject matter of the invention is the use of the substances of the invention in immunoassays. A particular subject matter of the invention is the use of the substances of the invention to increase the signal intensity and reduce false-negative analysis results in immunoassays. Experience has shown that the use of the substances of the invention or means in an immunoassay for antibodies significantly amplifies otherwise barely measurable signals when low antibody concentrations are present. The sensitivity of the immunoassay is increased so considerably that samples which would found to be negative without the substances of the invention can be identified as clearly antibody-positive. The signal increase can amount by a factor of 2–5. Such a drastic increase in the signal in antibody tests due to the use of the polymer substances in accordance with the invention was in so far surprising that the presence of the substances of the invention increases the viscosity of the incubation solution which in turn reduces the diffusion of the antibodies and antibody antigen complexes to the wall. One would then expect a lower signal in the test.

Yet, another subject matter of the invention is a method for preparing the substances in accordance with the invention. It is characterized in that in a first step, a protein, preferably albumin, especially bovine serum albumin is aggregated in a chemical aggregation reaction with bifunctional linkers; the chemical aggregation reaction preferably being a thermal aggregation reaction. The preferred particle size ranges between 10 and 200 nm, particularly preferred between 20 and 50 nm. Thermal aggregation is preferably carried out at a temperature between 50 and 100° C., more particularly between 60 and 80° C. Acylation with a —CO—R—group is then carried out in a second step with the aid of a suitable acylation agent. The acylation should preferably be completed and can be monitored via the use of acylation agent via HPLC, for example.

However, it is also possible that the method be carried out inversely by acylating protein according to U.S. Pat. No. 5,051,356 followed by thermal and chemical polymerization of the acylated protein.

EXAMPLE 1

Figure 1:
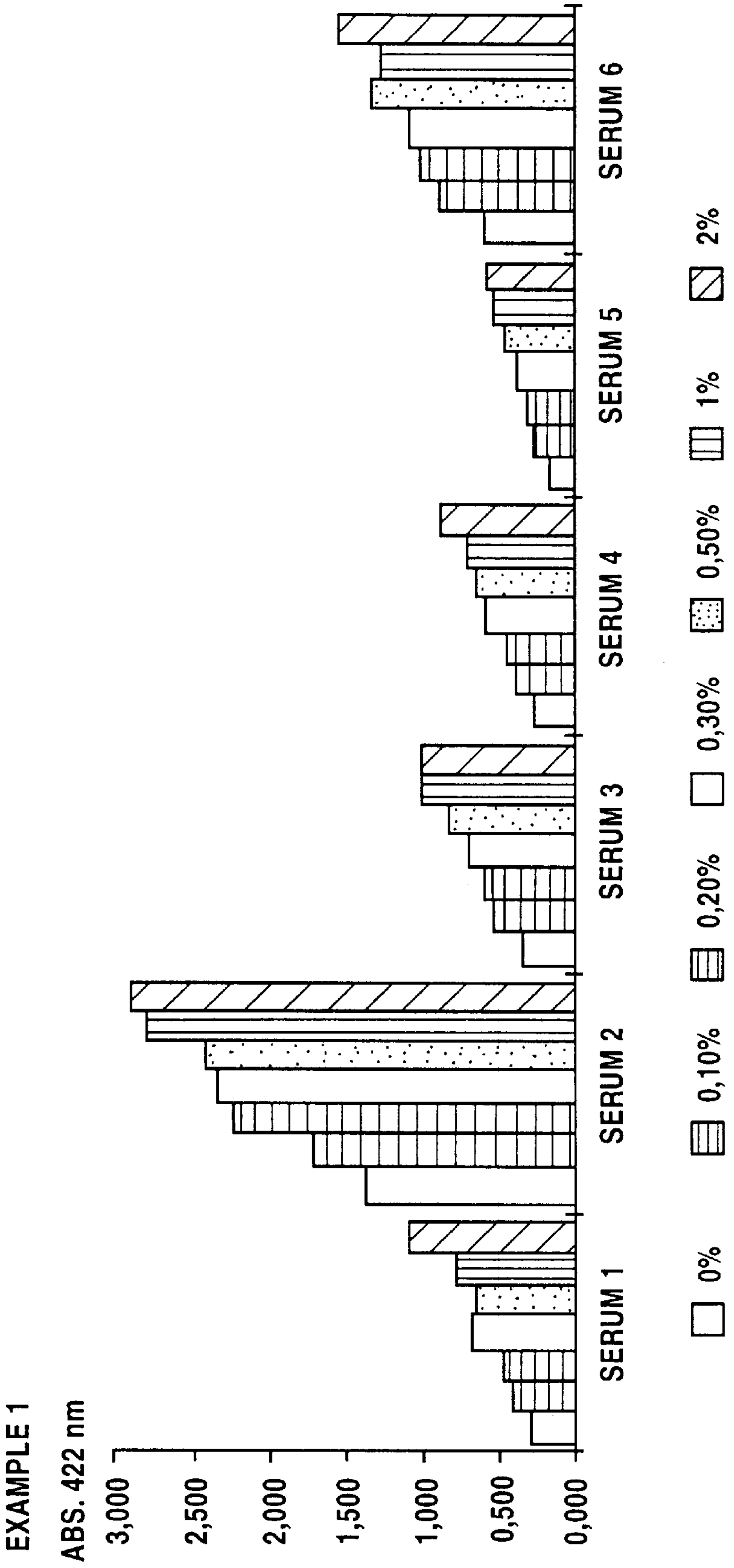
FIG. 1 illustrates the influence of increasing concentrations of acetylated thermo-BSA on the measurements of the samples 1–4. The signals significantly increase with a rising concentration of acylated thermo-BSA while the blank value remains the same. The result is significantly increased sensitivity.
Figure 2:
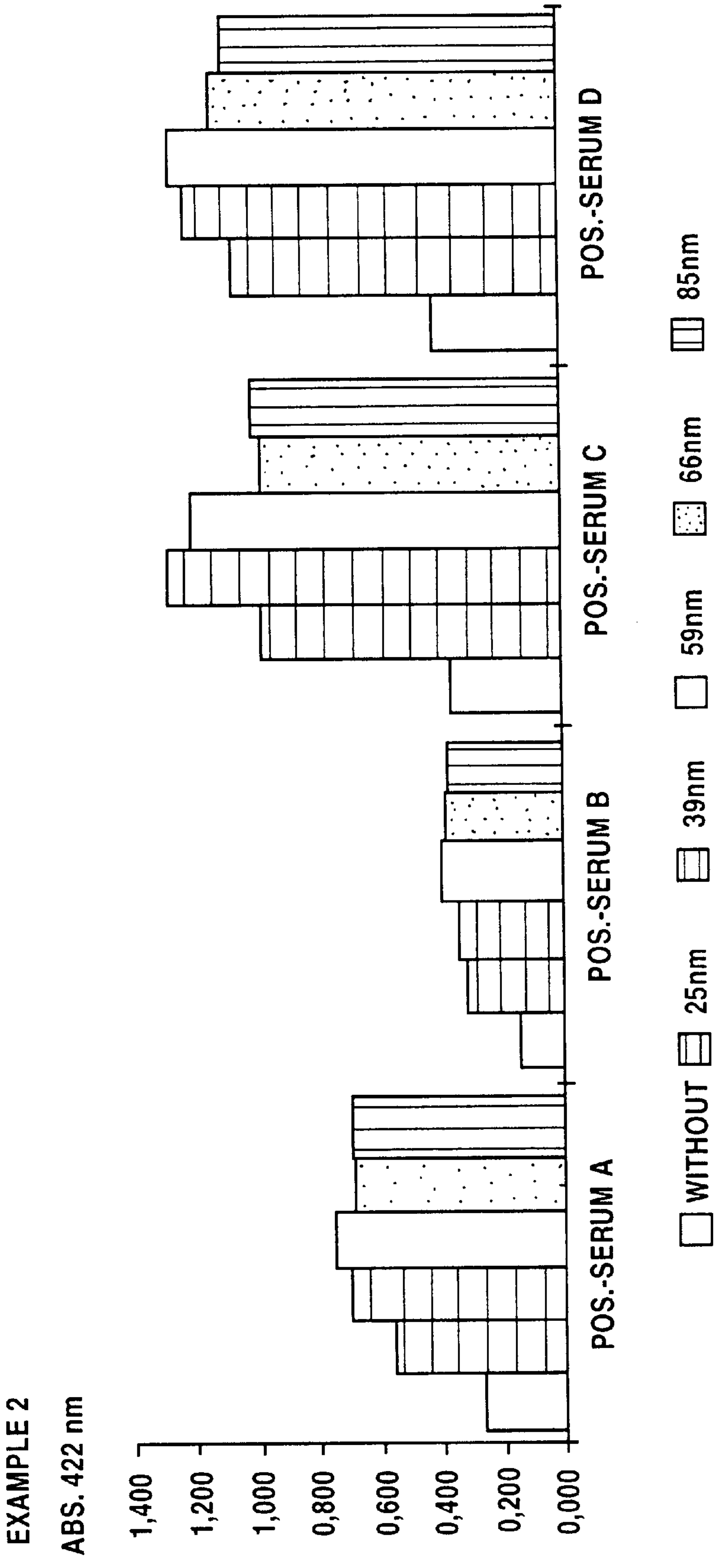
FIG. 2 shows the results of an anti-HCV test with acetylated thermo-BSA of different particle sizes.
Figure 3:
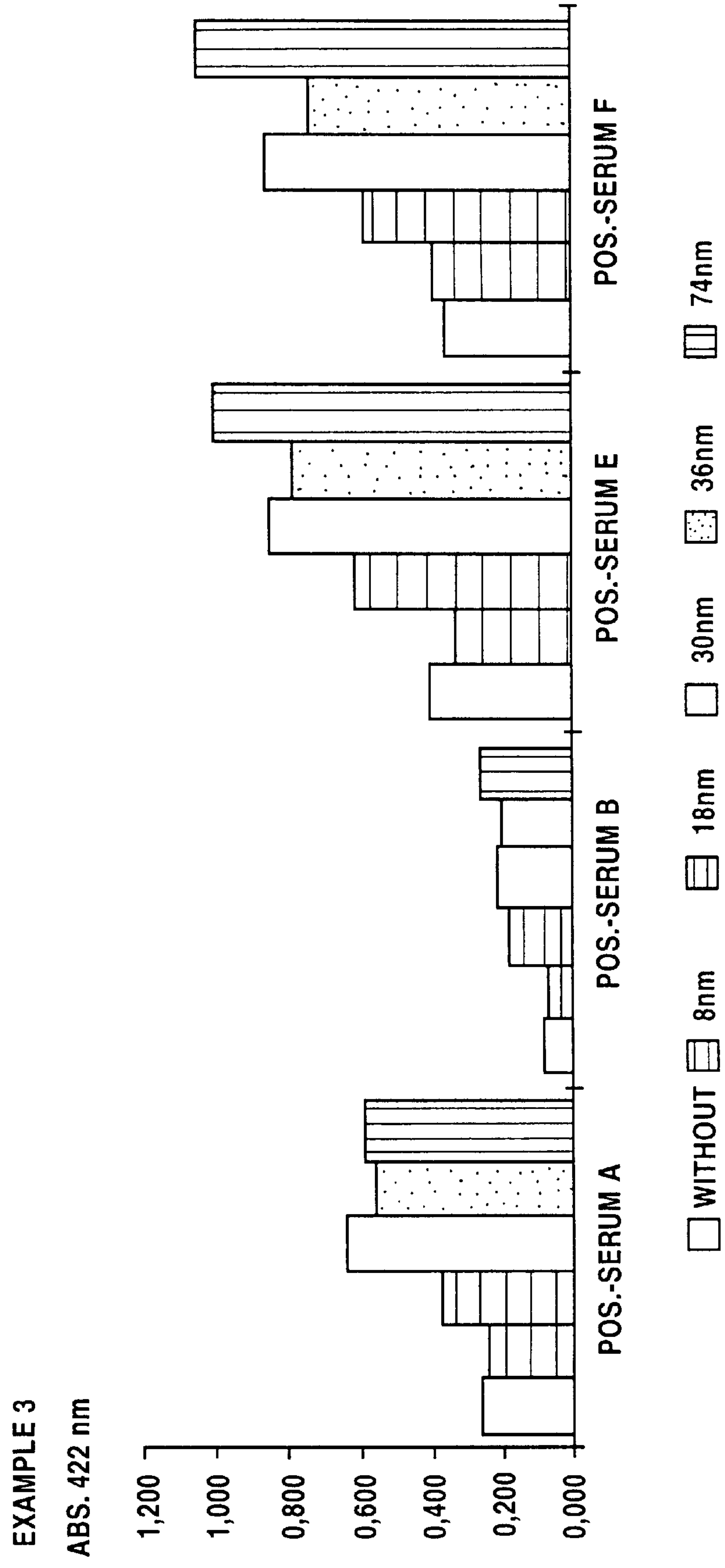
FIG. 3 shows the results of an anti-HCV test with succinylated thermo-BSA of different particle sizes.

Influence of Acetylated Thermo-BSA on the Signals of HCV-Positive Sera

Sandwich immunoassay for anti-HCV with an ENZYMUN-TEST® (enzyme immunoassay) manufactured by Boehringer Mannheim:

1. Incubation buffer
   - Sodium phosphate 40 mmol/l, pH 7.4
   - Sodium chloride 7.1 g/l
   - N-methylisothiazolone-HCl 1 g/l
   - 2-chloracetamide 1 g/l
   - Plasma-diagnostic-based 210 ml/l
   - Biotinylated HCV peptides (5–100 ng/l, depending on the antigen)
   - Acetylated thermo-BSA in different concentrations between 0 and 1% (0.1%=1 mg/ml), particle size 30 nm
2. Conjugate buffer solution
   - Phosphate buffer 40 mmol/l, pH 7.0
   - Bovine albumin, 1 g/l
   - Bovine IgG 4 g/l
   - TRITON X (+Octylphenoxypolyethoxyethanol) 100 1 g/l
   - Anti-human-Fcγ-antibody (sheep)-POD
3. Substrate buffer
   - Phosphate/citrate 10 mmol/l, pH 4.4
   - $H_2O_2$ 3.2 mmol/l, ABTS 1.2 mmol/l The tests with the samples 1–4 are carried out on an ES 600 instrument by Boehringer Mannheim GmbH.

1st step: 1 hour: incubation of 20 μl sample+0.5 ml incubation buffer in a streptavidin-coated tube 2nd step: 1 hour: addition of 0.5 ml conjugate buffer with conjugate Washing step 3rd step: 1 hour incubation with 0.5 ml substrate buffer with chromogen.

Measurement of the substrate solution at 422 nm.

Table 1 illustrates the influence of increasing concentrations of acetylated thermo-BSA on the measurements of the samples 1–4. The signals significantly increase with a rising concentration of acetylated thermo-BSA while the blank value remains the same. The result is a significantly increased sensitivity.

TABLE 1

ES 600: signals at 422 nm (absorbances)

| Samples | Addition of acetylated TBSA in the incubation buffer | | | | | | |
|---|---|---|---|---|---|---|---|
| | 0% | 0.10% | 0.20% | 0.30% | 0.50% | 1% | 2% |
| Serum 1 | 0.294 | 0.414 | 0.475 | 0.684 | 0.689 | 0.805 | 1.108 |
| Serum 2 | 1.390 | 1.735 | 2.247 | 2.360 | 2.440 | 2.820 | 2.921 |
| Serum 3 | 0.369 | 0.562 | 0.608 | 0.709 | 0.859 | 1.026 | 1.032 |
| Serum 4 | 0.260 | 0.387 | 0.452 | 0.596 | 0.656 | 0.723 | 0.889 |
| Serum 5 | 0.172 | 0.275 | 0.310 | 0.390 | 0.479 | 0.553 | 0.580 |
| Serum 6 | 0.596 | 0.894 | 1.038 | 1.092 | 1.350 | 1.287 | 1.563 |

EXAMPLE 2

Anti-HCV Test with Acetylated Thermo-BSA of Different Particle Sizes

The test is carried out according to example 1, however, the incubation buffer contains 5 mg/ml acetylated thermo-BSA of different particle sizes ranging between 25 nm and 85 nm.

The results are shown in Table 2.

While there is no signal increase in HCV-negative sera, a significant signal increase can be seen when acetylated thermo-BSA of different particle size is used.

TABLE 2

ES 600: signals at 422 nm (absorbances)

| Samples | Addition of acetylated TBSA in the incubation buffer | | | | | |
|---|---|---|---|---|---|---|
| | without | 25 nm | 39 nm | 59 nm | 66 nm | 85 nm |
| Pos.-Serum A | 0.276 | 0.561 | 0.706 | 0.750 | 0.699 | 0.702 |
| Pos.-Serum B | 0.150 | 0.332 | 0.357 | 0.409 | 0.413 | 0.398 |
| Pos.-Serum C | 0.379 | 0.996 | 1.306 | 1.221 | 1.006 | 1.024 |
| Pos.-Serum D | 0.432 | 1.094 | 1.249 | 1.292 | 1.158 | 1.119 |
| Neg.-Serum 1 | 0.043 | 0.045 | 0.046 | 0.047 | 0.049 | 0.046 |
| Neg.-Serum 2 | 0.043 | 0.041 | 0.043 | 0.044 | 0.044 | 0.046 |
| Neg.-Serum 3 | 0.041 | 0.042 | 0.046 | 0.048 | 0.047 | 0.045 |
| Neg.-Serum 4 | 0.042 | 0.043 | 0.045 | 0.046 | 0.044 | 0.043 |
| Neg.-Serum 5 | 0.038 | 0.041 | 0.041 | 0.040 | 0.042 | 0.041 |

EXAMPLE 3

According to example 2, however, with succinylated thermo-BSA of different particle sizes used in the incubation buffer.

TABLE 3

ES 600: signals at 422 nm (absorbances)

| Samples | Addition of acetylated TBSA in the incubation buffer | | | | | |
|---|---|---|---|---|---|---|
| | without | 8 nm | 18 nm | 30 nm | 36 nm | 74 nm |
| Pos.-Serum A | 0.256 | 0.240 | 0.364 | 0.652 | 0.570 | 0.593 |
| Pos.-Serum B | 0.083 | 0.080 | 0.178 | 0.216 | 0.210 | 0.260 |
| Pos.-Serum E | 0.407 | 0.330 | 0.619 | 0.858 | 0.797 | 1.009 |
| Pos.-Serum F | 0.357 | 0.389 | 0.593 | 0.864 | 0.753 | 1.059 |
| Neg.-Serum 6 | 0.010 | 0.013 | 0.013 | 0.022 | 0.022 | 0.021 |
| Neg.-Serum 7 | 0.012 | 0.017 | 0.018 | 0.027 | 0.026 | 0.028 |
| Neg.-Serum 8 | 0.011 | 0.019 | 0.017 | 0.029 | 0.027 | 0.034 |
| Neg.-Serum 9 | 0.010 | 0.015 | 0.015 | 0.021 | 0.024 | 0.026 |
| Neg.-Serum 10 | 0.013 | 0.018 | 0.018 | 0.033 | 0.027 | 0.035 |

EXAMPLE 4

Preparation of Acetylated Thermally Aggregated Bovine Serum Albumin (Acetylated Thermo-BSA).

1. Preparation of Thermally Aggregated BSA 1 g BSA is heated up to 70° C. in 100 ml of 50 mM potassium phosphate buffer solution (pH 7.0) and maintained at this temperature for 4 hours. The solution is then cooled down, filtered, and concentrated to 50 mg/ml with the aid of an ultracentrifuge (exclusion limit: 30,000 Da). Then dialysis is carried out against the 30-fold volume of redistilled water followed by lyophilization. The resulting product has a molecular weight of approximately 700,000 and a particle size of 30±8 nm (measured via photon correlation spectroscopy (PCS)).

2. Acetylation of Thermo-BSA 4000 g of thermally aggregated BSA in 100 mM potassium phosphate buffer pH 8.0 are heated up to 25° C. The protein concentration is determined via OD 280 nm and then the protein concentration of 10 mg/ml is adjusted. If necessary, 10 mM potassium phosphate buffer pH 8.0 can be used to adjust the correct value. The thermo-BSA solution is poured into a stirring vessel and heated up to 25° C. Acetic acid in hydroxysuccinimide ester at a concentration of 100 mg/ml is dissolved in water-free DMSO at room temperature. 11.5 ml succinimide ester solution are added per liter of acetylated thermo-BSA solution. The so-obtained final concentration in DMSO amounts to approximately 1%. After checking the pH value (target 6.5–9), the acetylation mixture is stirred at 25° C. for 120 min. The decrease in acetic acid N-hydroxysuccinimide ester is monitored via TSK 3000/HPLC (detection at 260 nm). After incubation, the acetylation process is stopped by adding lysine hydrochloride solution to a final concentration of 5 mM.

The stopped acetylation reaction is filtered via a filter press. The press is subsequently washed with water. Filtrate and washings are then combined.

The combined filtrate is concentrated via a polysulfone membrane 10 KD to 50 l. Concentrated solution is diafiltrated against the 10-fold volume 20 mM potassium phosphate solution pH 7.0. The concentrate is then diluted to twice the volume using diafiltration buffer and then again concentrated to the initial volume. The result of the diafiltration is determined via TSK 3000 HPLC analysis. The solution is concentrated to 80±10 mg/ml and subsequently stabilized with 0.1% chloracetamide and 0.01% MIT (methylisothiazolone).

The PCS measurement gave a particle size of 30 nm±15.

EXAMPLE 5

Preparation of Chemically Polymerized, Acetylated Bovine Serum Albumin (P-RSA-Succ)

1. Polymerizing bovine serum albumin (BSA)
   a) Activation of BSA with maleinimidohexanoyl-N-hydroxysuccinimide (MHS)

3 g BSA are dissolved in 30 ml of 30 mM potassium phosphate buffer, pH 7.1, and 0.6 ml of a solution of 180 mg MHS/ml dimethylsulfoxide (DMSO) are added. After 1 hour incubation at 25° C., the solution is spiked up to 10 mM lysine and dialyzed against the 150-fold volume dialysis buffer (15 mM potassium phosphate buffer/50 mM NaCl/1 mM ethylenediamine tetraacetate (EDTA)/pH 6.2).

b) Activation of BSA with S-acetylthiopropionyl-N-hydroxysuccinimide (SATP)

3 g BSA are dissolved in 30 ml of 30 mM potassium phosphate buffer and 0.6 ml of a solution of 140 mg SATP/ml DMSO are added. After 1 hour incubation at 25° C., the solution is spiked up to 10 mM lysine and dialyzed against the 150-fold volume of dialysis buffer (15 mM potassium phosphate buffer/50 mM NaCl/1 mM EDTA/pH 6.2).

c) Polymerizing the activated BSA components

The solution with the SATP-activated BSA from (b) is spiked up to 25 mM hydroxylamine, a pH of 7.5 is adjusted, and incubation is carried out for 1 hour at 25° C. Subsequently, the solution with the MHS-activated BSA from (a) is added, and incubation is continued for another 45 minutes at 25° C. Polymerization is stopped by adding 10 mM cysteine. After another 30 minutes, the solution is spiked up to 25 mM N-methylmaleinimide and dialyzed against the 150-fold volume of 50 mM potassium phosphate buffer/0.15 M NaCl/pH 7.2.

2. Succinylation 2.6 ml of the solution of 0.1 g succinic acid anhydride/ml DMSO are added to the dialyzed poly-BSA solution from (1). After incubation for 60 min at 25° C., the solution is spiked up to 50 mM lysine, dialyzed against the 150-fold volume of 20 mM potassium phosphate buffer, pH 6.8, and lyophilized.

We claim:

1. A method for determining the presence of an antibody in a sample wherein said method avoids false negative results and increases signal intensity, comprising the steps of contacting a sample to be tested for an antibody with at least one specific binding partner of the antibody in the presence of a protein aggregate which is acylated with —CO—R groups, wherein R is a branched or unbranched C1–C4 alkyl residue which is unsubstituted or substituted with a member selected from the group consisting of carboxy, hydroxy, $SO_3H$ and $PO_3H_2$, and wherein at least one specific binding partner is labeled, to form a detectable binding pair, and measuring the signal of the detectable binding pair or any unbound specific binding partner as a measure of the presence or concentration of said antibody in the sample, wherein the particle size of the acylated protein aggregate is between 10 and 200 nm.

2. The method according to claim 1, wherein the antibody is directed against a virus.

3. The method according to claim 1, wherein an unlabeled binding partner which is an antigen capable of binding to the antibody to be determined is used in addition to the labeled specific binding partner.

4. The method according to claim 1, wherein the labeled binding partner is an anti-antibody.

5. The method according to claim 3, wherein the sample and the unlabeled binding partner are first brought into contact with said acylated protein aggregate and the labeled binding partner is subsequently added.

6. The method according to claim 3, wherein the unlabeled binding partner has a second binding site for a solid phase-bound binding partner.

7. The method according to claim 6, wherein the unlabeled binding partner is biotinylated.

8. A method for increasing the intensity of a signal and avoiding false negatives in an immunoassay, comprising contacting a protein aggregate which is acylated with —CO—R groups, wherein R is a branched or unbranched C1–C4 alkyl residue which is unsubstituted or substituted with a member selected from the group consisting of carboxy, hydroxy, $SO_3H$ and $PO_3H_2$, with at least one specific binding partner used in said immunoassay, wherein the particle size of the acylated protein aggregate is between 10 and 200 nm.

9. A method for determining the presence or concentration of an analyte in a sample, said method comprising contacting the sample to be tested with at least one specific binding partner of the analyte in the presence of a protein aggregate which is acylated with —CO—R groups wherein R is a branched or unbranched $C_1$–$C_4$ alkyl residue which is unsubstituted or substituted with a member selected from the group consisting of carboxy, hydroxy, $SO_3H$ and $PO_3H_2$, wherein at least one specific binding partner is labeled, to form a detectable binding pair, and measuring the signal of the detectable binding pair or any unbound specific binding partner as a measure of the presence or concentration of said analyte in the sample, wherein the particle size of the acylated protein aggregate is between 10 and 200 nm.

* * * * *